United States Patent [19]

Azria et al.

[11] Patent Number: 5,149,537
[45] Date of Patent: Sep. 22, 1992

[54] USE OF TAUROCHOLIC ACID AND ITS SALTS AS ENHANCERS FOR CALCITONIN CONTAINING PHARMACEUTICAL COMPOSITIONS

[75] Inventors: Moise Azria, Basel; Michel Steiger, Berne, both of Switzerland

[73] Assignee: Sandoz Ltd., Basel, Switzerland

[21] Appl. No.: 791,841

[22] Filed: Nov. 14, 1991

Related U.S. Application Data

[63] Continuation of Ser. No. 497,036, Mar. 21, 1990, abandoned, which is a continuation of Ser. No. 243,576, Sep. 13, 1988, abandoned.

[30] Foreign Application Priority Data

| Sep. 15, 1987 [GB] | United Kingdom | 8721700 |
| Jan. 29, 1988 [GB] | United Kingdom | 8801991 |
| Mar. 3, 1988 [GB] | United Kingdom | 8805068 |

[51] Int. Cl.$^5$ .................. A61K 37/00; A61K 37/24
[52] U.S. Cl. .................. 424/436; 514/966; 514/808; 514/21; 514/2; 424/433
[58] Field of Search .................. 424/433, 436; 514/2, 514/21, 808, 966

[56] References Cited

U.S. PATENT DOCUMENTS

| 4,156,719 | 5/1979 | Sezaki | 514/8 |
| 4,164,573 | 8/1979 | Galinsky | 514/3 |
| 4,434,159 | 2/1984 | Sekine et al. | 424/178 |
| 4,438,052 | 3/1984 | Weder | 514/2 |
| 4,731,210 | 3/1988 | Weder | 436/829 |
| 4,801,577 | 1/1989 | Nestor, Jr. | 514/15 |

OTHER PUBLICATIONS

D. Thiebaud, et al., Amer. J. Med. 82, 745-750 (1987).
E. Ziv, et al., Life Sciences, vol. 29, pp. 803-809 (1981).

Primary Examiner—Thurman K. Page
Assistant Examiner—A. Hulina
Attorney, Agent, or Firm—Gerald D. Sharkin; Robert S. Honor; Carl W. Battle

[57] ABSTRACT

Suppositories comprising a suppository base, a calcitonin and taurocholic acid or a pharmaceutically acceptable salt thereof exhibit improved bioavailability and are well tolerated.

20 Claims, No Drawings

USE OF TAUROCHOLIC ACID AND ITS SALTS AS ENHANCERS FOR CALCITONIN CONTAINING PHARMACEUTICAL COMPOSITIONS This is a continuation of application Ser. No. 07/497,036, filed Mar. 21, 1990 which in turn is a continuation of application Ser. No. 07/243,576, filed Sep. 13, 1988, both now abandoned.

This invention relates to calcitonins and to the use of taurocholic acid or a pharmaceutically acceptable salt thereof as an enhancer for suppositories.

The calcitonins comprise a known class of pharmaceutically active, long-chain polypeptides of varying, well-documented pharmaceutical utility. They lower calcium levels in the blood and are commonly employed in the treatment of e.g. Paget's disease, hypercalcemia and osteoporosis. They may be naturally occurring and be prepared by extraction from natural sources or by synthesis (including by genetic engineering).

The term calcitonin embraces calcitonins which are naturally occurring (whether extracted or produced synthetically) and derivatives and analogs having a hypocalcemic activity or calcitonin-like activity. Derivatives and analogs include in particular natural calcitonin structures, wherein one or more amino-acid radicals are replaced by one or more other amino-acid radicals and/or the S-S-bridge is replaced by an alkylene bridge, and/or is opened and/or wherein one or several amino acid radicals have been omitted, and/or wherein the N- or C-terminal is modified, and/or the ring has been opened.

The usual form of administration is by injection. We have now found that particular suppository compositions provide an especially convenient form of calcitonin administration. More particularly we have surprisingly found that in accordance with the particular teachings of the present invention, calcitonin plasma profiles equivalent to those obtained on administration of standard intra-muscular doses can be achieved on administration with the suppository compositions of the invention at dosage levels which are fully within the limits of tolerability and practicability.

Various proposals have been made before for calcitonin suppositories using enhancers, but none of these have been marketed before the date of this invention.

For example, UK Patent 1,354,525, dated April 1970, discloses a variety of galenical formulations of fish calcitonin (e.g. salmon calcitonin), including a nebulizer composition, a nasal composition, a sublingual glosset, a topical cream and a suppository composition. A single example is given of a suppository. The suppository base contained lactose, polyethylene glycol 400 and 4,000, polysorbate 80 (polyoxyethylene (20) sorbitan monooleate) and glycerin, and is buffered with lactic acid to pH 4.5. No further details were given of the exact composition.

Various proposals have also been used to increase the rectal absorption of active agents using enhancers such as surfactants. There is however, no generally applicable system.

After exhaustive animal and clinical testing, we have found that well tolerated suppositories with exceptionally interesting bioavailability and stability may be made, incorporating the previously unrecognized and unapproved enhancer, taurocholic acid or a salt thereof, especially sodium taurocholate.

The present invention provides a suppository comprising a suppository base, a calcitonin and taurocholic acid or a pharmaceutically acceptable salt thereof.

The calcitonin is preferably human, salmon or eel (Asu 1-7 eel) calcitonin, or a calcitonin derivative or analog thereof, more preferably eel or salmon calcitonin, especially salmon calcitonin.

The calcitonin may be used in free base form, pharmaceutically acceptable acid addition salts form, or complex form. Acid addition salt may be formed with e.g. organic acids, including polymeric acids and inorganic acids. Such acid addition salt forms include e.g. the acetates and hydrochlorides. By complexes are to be understood those formed on addition of inorganic substances, e.g. inorganic salts or hydroxides such as Ca- and Zn-salts, and/or an addition of polymeric organic substances.

The calcitonin may be used e.g. in the form of a polyacetate, polyhydrate or in free base form. Typical activities are for example for salmon calcitonin from about 4,500 to about 5,500 I.U./mg.

As suppository base may be used cocoa butter. It is preferred to use synthetic or semi-synthetic suppository bases. These may be water insoluble fats, e.g. glycerides (mono-, di- and/or tri-) of fatty acids, e.g. made from coconut oil or palm kern oil.

Straight Chain $C_{10-18}$ fatty acid glycerides, conveniently saturated are preferred. Examples are Witepsol (Registered Trade Mark), e.g. Witepsol H series available from Dynamit Nobel, W. Germany; Suppocire (Registered Trade Mark), e.g. Suppocire AM or AS2, available from Gattefosse, France and Novata (Registered Trade Mark), e.g. Novata BD, available from Henkel GmbH, W. Germany.

Alternatively, the Guerbet alcohols and water soluble suppository bases such as polyethyleneglycol may be used.

Preferably the suppository base has a low melting range, e.g. 30 to 36° C.

The Taurocholic acid preferably contains less than 10%, more preferably less than 7%, particularly less than 5%, of cholic acid impurities as determined by analysis. Preferably the taurocholic acid should be free from or contain less than 1 per cent of deoxycholic acid and its derivatives. The taurocholic acid should preferably contain less than 5 per cent cholic acid or its salts.

If desired the taurocholic acid may be present as a salt, e.g. the potassium, the barium or especially the sodium salt.

The taurocholic acid may, if desired, have some crystalline character or be amorphous.

Preferably the suppositories contain from 1 to 4 per cent by weight of taurocholic acid or a pharmaceutically acceptable salt thereof, e.g. the sodium salt, preferably 1.8 to 2.1 per cent, particularly 2 per cent by weight, e.g. 15 to 60 mg per dose.

The suppositories according to the invention preferably include a buffer to provide a pH of from 3.8 to 5.0 e.g. 3.8 to 4.8, particularly 4.4. A preferred buffer is a citric acid/sodium citrate buffer system.

The suppositories of the invention may contain further ingredients such as water soluble diluents, e.g. mannitol or lactose. These may be present in an amount of from 1 to 10%, e.g. 2 to 5 per cent, by weight of the suppository.

The suppositories may be made e.g. by mixing the ingredients and converting the resulting mixture into suppositories. They may be produced by conventional mold casting processes. For example one or more of the ingredients, e.g. the ingredients other than the suppository base, may be mixed e.g. with liquid such as water, to form a granulate, which may then be dried. The dried mass may then be mixed with molten suppository base. The temperature of the molten mass should preferably be kept low, e.g. below 40° C. to avoid degradation of the calcitonin. Alternatively a low temperature compression process may be used, e.g. as described in UK Patent No. 2,030,861. A dry granulate based on calcitonin is made, then mixed with taurocholic acid and the suppository base and this is compressed into suppositories, e.g. in a tabletting machine filled with appropriate molds and a low temperature cooling system, e.g. at 10 or 5° C. or below.

Suppositories are preferably from 1 to 2 grams in weight. The especially preferred weight is 1.0 to 1.5 g, e.g. 1.5 g. The suppositories according to the invention are useful for the same indications known for parenterally administered calcitonins.

The exact dose of calcitonins and taurocholic acid administered may be ascertained through comparative clinical, rabbit, dog and other animal bioavailability studies using known parenteral forms of calcitonin as the standard. We have found that a particularly good animal model is based on the use of New Zealand rabbits (weight ca. 2.5-4 kg) which have been fasted for 5 days. Blood is taken at intervals over 7 hours. The calcitonin content measured by standard methods, e.g. radioimmunoassay methods, or the calcium levels are measured by the calcium ion selective electrode method.

Rabbit studies show that the suppositories of the invention have unexpectedly good bioavailability, e.g. compared to polysorbate 80 and other cholic acid derivatives as enhancer. For example the AUC (Area Under the Curve) over 2 hours and Cpmax with sodium taurocholate are at least twice the AUC and Cpmax when sodium glycocholate is used as enhancer. Moreover, calcitonin levels can be detected in the blood in a very short time for example within 10 minutes of administration.

Clinical studies may be effected to show the bioavailability in man up to 1 hour or more than 1 hour after administration. Clinical tolerability studies may be effected over 3 days. These show that the suppositories of the invention are well tolerated.

In general, the suppositories of the invention have a bioavailability from 2 to 6 times less than that of the corresponding parenteral intra-muscular dose. Bioavailability per unit of calcitonin in the suppositories of the invention, in general, increases with a decreasing total calcitonin dose.

The suppositories for salmon calcitonin preferably contain 50, 100, 200 or 300 I.U. of salmon calcitonin, e.g. 200 or 300 I.U.

The suppositories of the invention are indicated for twice-a-day or preferably once-a-day administration.

Accordingly, the invention also provides:

a) use of taurocholic acid or a pharmaceutically acceptable salt thereof in the manufacture of a suppository to administer a calcitonin;

b) a method of administering a calcitonin to a subject requiring treatment therewith, comprising administering a suppository as defined above.

In the following examples all temperatures are in degrees Centigrade and are uncorrected.

Taurocholic acid or the sodium salt used contained less than 7% of impurities on analysis, e.g. less than 1% deoxycholic acid derivatives and less than 5% sodium cholate. The brand used is from Fluka, Switzerland, or preferably Calbiochem, Lucerne, Switzerland.

Suppository Base A is Witespol H 12. Melting range 32-33.5° C. Solidification range 29-33° C.

Suppository Base B is Witespol H 15. Melting range 33.5-35.5° C. Solidification range 32.5-34.5° C.

Further details of the excipients may be found in H. P. Fiedler Lexikon der Hilfsstoffe, 2nd Edition, Edito Cantor Aulendorf 1982, or manufacturer's literature.

Wire screens used for sieving are stainless steel sieves. Aperture size (hereinafter AS) is based on ISO 2194-1972 (R10); wire diameter (hereinafter WD) is based on DIN 4189.

PREPARATION EXAMPLE 1

Suppositories containing 300 I.U. (International Units) of salmon calcitonin are prepared containing the following composition per suppository:

| Ingredient | mg/Suppository |
| --- | --- |
| Salmon calcitonin (300 I.U.) | 0.0692⁻ |
| Anhydrous citric acid | 0.78 |
| Trisodium citrate dihydrate | 0.50 |
| Mannitol | 48.651 |
| Sodium taurocholate | 30.0 |
| Suppository base A | 1420.0 |
| | 1500 mg |

⁻ 1 mg substance contains 4767 I.U. (overage of 10 percent used)

Preparation procedure a) Preparation of granulate (for 3,500 doses)

0.2423 g of the calcitonin, 2.73 g of the citric acid, 1.75 g of the tri-sodium salt are mixed in the dry state and dissolved in 14.0 g water. 170.3 g of sieved mannitol is added (AS 700 microns, WD 120 microns). The mass is kneaded and sieved (AS 1,600 microns, WD 450 microns). The des-agglomerated powder is dried at 40° C. for 25 minutes, and sieved (AS 450 microns, AS 120 microns) to give 167 g of a powder.

b) Addition of enhancer and molding (for 3,000 doses)

150 g of the powder obtained from step a) and 90 g of ground sodium taurocholate as mixed, sieved (AS 250; WD 100 microns), and mixed again. The mixture is added to 4260 g of melted suppository base A at 38° C. Homogenization is effected (Polyton apparatus, speed setting 4) for 3 minutes. The mass is transferred at 33° C. to a pre-warmed vessel in a suppository making machine (BONAPACE).

The suppositories are molded at from 33 to 33.5° C. in neutral polyvinylchloride foil (or aluminium foil) in doses of about 1.5 ml and weight 1.5 g. Cooling is effected with an air stream at 20° C. Yield 2,590 suppositories. Disintegration time 6 minutes. Melting point 34.9° C. Hardness 81N at 20° C. pH in water 4.2.

PREPARATION EXAMPLE 2

Suppositories are prepared containing per suppository:

| Ingredient | mg/Suppository |
| --- | --- |
| Salmon calcitonin (300 I.U.) | 0.064⁻ |
| Crystalline Citric acid | 0.85 |
| Tri-sodium citrate dihydrate | 0.50 |
| Mannitol | 48.586 |
| Taurocholic acid* | 45.0 |

-continued

| Ingredient | mg/Suppository |
|---|---|
| Suppository Base A (Powder) | 1405.0 g |
| | 1500 mg |

*or sodium salt
** 1 mg substance contains 4963 I.U.

A charge is made up as follows:

Preparation of granulate (for 11,500 doses)

In a glass vessel 9.78 g citric acid, 5.75 g trisodium citrate dihydrate, 0.736 g salmon calcitonin are dissolved in 60 g demineralized water. 559 g Mannitol sieved (AS 1,600 microns; WD 450 microns) are added. The mass is mixed, kneaded and sieved (AS 1,600 microns; WD 450 microns) and the resultant granulate is dried in an air temperature of 50° C. The granulate is sieved again (AS 450 microns; WD 120 microns).

Addition of enhancer (for 10,400 doses)

525 g of the resultant granulate is mixed with 472.5 g taurocholic acid. The mass is sieved (AS 1,000 microns; WD 450 microns). 14.612 kg of suppository base is added to 988 g of the above mixture. The mass is mixed and sieved (AS 1,600 microns; WD 450 microns). The granulate is further mixed to produce uniform particles at a temperature rising from 6° C. to 23° C. over 5 minutes. The mass is then sieved first through a coarse sieve (AS 3,000 microns; WD 1,600 microns) and then through a fine sieve (AS 1,600 micron; WD 450 microns) to give a granulate for compression.

Compression

The resultant granulate is fed into a cooled rotary tabletting press filled with molds for suppositories (e.g. Fette P.2000 Cooltex) and fitted with Teflon covered punch die. Compression is effected at 5° C. to give suppositories weighing 1.5 g.

Stability

At least 2 years at 5° C.

Bioavailability

From the rabbit model, bioavailability (AUC) is of the same order as a 100 I.U. i.m. injection.

Further suppositories are made containing 100 and 200 I.U. of salmon calcitonin and/or appropriate amounts of human, or Asu-1-7 eel calcitonin.

PREPARATION EXAMPLE 3

Suppositories are prepared as in Preparation Example 1 containing Suppository Base B instead of Suppository Base A.

PREPARATION EXAMPLE 4

A 200 I.U. salmon calcitonin 1 g suppository is made from calcitonin (0.0416 mg, 4804 I.U./mg), 0.78 mg citric acid, 0.5 mg tri-sodium citrate dihydrate, 48.678 mg mannitol, 20.0 mg sodium taurocholate and 905 mg suppository base A in analogous manner to example 1.

Bioavailability results in Rabbit model

The suppositories of Example 4 are administered to rabbits and the results obtained are:

| | |
|---|---|
| $C_{max}$ | 33.5 mI.U./ml |
| $t_{max}$ | 0.125 hours |

-continued

| | |
|---|---|
| AUC (0-2 hr) | 17.76 mI.U. ml$^{-1}$ · hr |

The bioavailability in this test is indicated to be significantly greater than that obtained with e.g. sodium glycocholate or polyoxyethylene cetyl ether and polysorbate 80 as enhancer.

What is claimed is:

1. A pharmaceutical composition in suppository form useful in reducing calcium levels in the blood and exhibiting enchanced bioavailability of the active ingredient comprising: 1) a suppository base; 2) as the active ingredient, a therapeutically effective amount of calcitonin in free base, pharmaceutically acceptable acid addition salt or complex form; and 3) as an enhancer for the calcitonin, from 1% to 4% of taurocholic acid, or a pharmaceutically acceptable salt thereof, based on the total weight of the composition.

2. A composition according to claim 1 wherein the enhancer is present in an amount of from 1.8% to 2.1%, based on the total weight of the composition.

3. A composition according to claim 1 wherein the enhancer is present in pharmaceutically acceptable salt form.

4. A composition according to claim 3 wherein the enhancer is the sodium salt of taurocholic acid.

5. A composition according to claim 1 wherein the active ingredient is selected from human, eel and salmon calcitonin.

6. A composition according to claim 5 wherein the active ingredient is salmon calcitonin.

7. A composition according to claim 1 which additionally contains a buffer in an amount so that the pH of the composition is between 3.8 and 5.0.

8. A composition according to claim 1 which additionally contains from 1% to 10% of a water soluble diluent, based on the total weight of the composition.

9. A composition according to claim 8 which contains from 2% to 5% of a water soluble diluent, based on the total weight of the composition.

10. A composition according to claim 8 wherein the water soluble diluent is mannitol or lactose.

11. A composition according to claim 6 containing 50 International Units of salmon calcitonin.

12. A composition according to claim 6 containing 100 International Units of salmon calcitonin.

13. A composition according to claim 6 containing 200 International Units of salmon calcitonin.

14. A composition according to claim 6 containing 300 International Units of salmon calcitonin.

15. A method of enhancing the bioavailability of calcitonin in calcitonin-containing suppositories comprising employing, as the enhancer, from 1% to 4% of taurocholic acid, or a pharmaceutically acceptable salt thereof, based on the total weight of the suppository.

16. A method according to claim 15 wherein the enhancer is present in an amount of from 1.8% to 2.1%, based on the total weight of the suppository.

17. A method according to claim 15 wherein the enhancer is present in pharmaceutically acceptable salt form.

18. A method according to claim 17 wherein the enhancer is the sodium salt of taurocholic acid.

19. A method according to claim 15 wherein the calcitonin is selected from human, eel and salmon calcitonin.

20. A method according to claim 19 wherein the calcitonin is salmon calcitonin.

* * * * *